(12) United States Patent
Ressler et al.

(10) Patent No.: US 8,125,333 B2
(45) Date of Patent: Feb. 28, 2012

(54) METHODS, SYSTEMS AND APPARATUS FOR MONOCHROMATIC UV LIGHT STERILIZATION

(75) Inventors: Barry Ressler, Danbury, CT (US); Bernard Anthony McNulty, Weston, CT (US)

(73) Assignee: Triton Thalassic Technologies, Inc., Ridgefield, CT (US)

( * ) Notice: Subject to any disclaimer, the term of this patent is extended or adjusted under 35 U.S.C. 154(b) by 457 days.

(21) Appl. No.: 12/475,902

(22) Filed: Jun. 1, 2009

(65) Prior Publication Data
US 2010/0007492 A1    Jan. 14, 2010

Related U.S. Application Data

(60) Provisional application No. 61/058,746, filed on Jun. 4, 2008.

(51) Int. Cl.
  *G08B 21/00* (2006.01)
  *H01J 9/16* (2006.01)
  *A61L 2/00* (2006.01)
  *C12N 13/00* (2006.01)

(52) U.S. Cl. ............... 340/540; 250/455.11; 250/492.1; 250/504 R; 250/494.1; 250/435; 422/24; 426/238; 426/248; 426/420; 435/173.3; 99/451

(58) Field of Classification Search .................. None
See application file for complete search history.

(56) References Cited

U.S. PATENT DOCUMENTS

| | | |
|---|---|---|
| 4,837,484 A | 6/1989 | Eliasson et al. |
| 4,866,282 A | 9/1989 | Miripol et al. |
| 4,952,812 A | 8/1990 | Miripol et al. |
| 5,013,959 A | 5/1991 | Kogelschaltz |
| 5,194,740 A | 3/1993 | Kogelschaltz et al. |
| 5,433,738 A | 7/1995 | Stinson |
| 5,446,289 A | 8/1995 | Shodeen et al. |
| 5,730,934 A | 3/1998 | Holbert |
| 5,786,598 A | 7/1998 | Clark |
| 5,843,374 A | 12/1998 | Sizer et al. |
| 5,922,278 A | 7/1999 | Chapman et al. |
| 5,955,840 A | 9/1999 | Arnold et al. |
| 6,190,608 B1 | 2/2001 | Laub et al. |
| 6,190,609 B1 * | 2/2001 | Chapman et al. ............... 422/24 |
| 6,194,821 B1 | 2/2001 | Nakamura |
| 6,201,355 B1 | 3/2001 | Morgan et al. |
| 6,730,923 B1 * | 5/2004 | May et al. .................. 250/494.1 |
| 7,057,189 B2 | 6/2006 | Coogan |
| 7,217,936 B2 | 5/2007 | Ressler |
| 7,282,358 B2 | 10/2007 | Coogan et al. |

(Continued)

OTHER PUBLICATIONS

PCT International Search Report dated Sep. 8, 2009.

*Primary Examiner* — Julie Lieu
(74) *Attorney, Agent, or Firm* — McCarter & English, LLP

(57) ABSTRACT

The present disclosure provides for methods, systems and apparatus for monochromatic UV light sterilization of container systems and/or container-packaged products. More particularly, the present disclosure provides for improved methods, systems and apparatus for monochromatic UV light sterilization of liquid and/or solid products/solutions and/or packaging/container systems for liquid and/or solid products/solutions (e.g., parenteral pharmaceutical products/solutions and/or packaging/container systems for parenteral pharmaceutical products/solutions). In exemplary embodiments, the present disclosure provides for improved systems and methods for the sterilization of container systems and/or container-packaged products using monochromatic, continuous wave, high-intensity, incoherent light in multiple light source configurations, wherein such sterilization regimen achieves a desired sterilization level without negatively affecting the physical properties of the package/container systems and/or the efficacy of the underlying products/systems.

38 Claims, 8 Drawing Sheets

U.S. PATENT DOCUMENTS

| | | |
|---|---|---|
| 8,021,608 B2 * | 9/2011 | Brown-Skrobot et al. ..... 422/22 |
| 2001/0035342 A1 * | 11/2001 | Morse et al. .................. 204/164 |
| 2002/0015662 A1 | 2/2002 | Hlavinka |
| 2002/0177118 A1 | 11/2002 | Coogan, Jr. et al. |
| 2004/0219056 A1 * | 11/2004 | Tribelsky et al. ................ 422/22 |
| 2005/0025662 A1 * | 2/2005 | Lestician ......................... 422/24 |
| 2005/0040336 A1 * | 2/2005 | Akkerman et al. ............ 250/343 |
| 2005/0173652 A1 * | 8/2005 | Ressler .................... 250/455.11 |

\* cited by examiner

METHODS, SYSTEMS AND APPARATUS FOR MONOCHROMATIC UV LIGHT STERILIZATION

CROSS REFERENCE TO RELATED APPLICATIONS

This application claims the benefit of U.S. Provisional Application No. 61/058,746 filed Jun. 4, 2008, all of which is herein incorporated in its entirety.

BACKGROUND

1. Technical Field

The present disclosure relates to methods, systems and apparatus for UV light sterilization of container systems and/or container-packaged products, and, more particularly, to systems and methods for monochromatic UV light sterilization of liquid and/or solid products/solutions and/or packaging/container systems for liquid and/or solid products/solutions (e.g., parenteral pharmaceutical products/solutions and/or packaging/container systems for parenteral pharmaceutical products/solutions).

2. Background Art

In general, sterilization is typically defined as the substantially complete destruction of all organisms, including a large number of highly resistant bacterial endospores. Several sterilization techniques have been developed to address specific sterilization needs. For example, some typical sterilization techniques include the use of moist heat from a steam autoclave, ethylene oxide gas sterilizing techniques, dry heat techniques, and newer chemical sterilizers.

One widely used sterilization technique is steam sterilization. In general, steam sterilization is typically viewed as being relatively cost-effective. For example, steam sterilization techniques employing an autoclave are recognized as efficient, simple, and relatively cost-effective approaches for destroying relevant organisms. However, certain components (e.g., some packaging/container system materials and/or products; medical device/instrumentation components and accessories) cannot endure the extremes of heat and/or pressure. For example, steam and pressure are known to risk damage to rubber, Lexan® polycarbonate components, and other synthetic materials. In addition, the use of steam autoclave techniques for anesthesia equipment is generally not recommended, unless the treatment method is specifically recommended by the manufacturer. Moreover, steam sterilization techniques are not readily incorporated into an in-line (i.e., continuous or substantially continuous) process, such as, for example, a packaging/container system filling process. Additionally, typical steam sterilization techniques increase energy costs and generate waste products.

Ethylene oxide is acceptable for many materials used in manufacturing medical devices and the like, such as, for example, the reusable components of anesthesia machines, ventilators, and monitors. However, it is generally inappropriate to place these entire systems in an ethylene oxide chamber. In addition, polystyrene component parts generally should not be exposed to ethylene oxide gas. In general, ethylene oxide sterilization employs a powerful poisonous fumigant gas, and therefore mandates an appropriate means of aeration to remove residual gas. Ethylene oxide has been classified as carcinogenic to humans by the International Agency for Research on Cancer (IARC), and is known to be explosive. Workers exposed to ethylene oxide are required to comply with all procedures specified by OSHA and the EPA.

Alternatively, other chemical treatment techniques include the use of hydrogen peroxide and peroxyacetic acid with buffers and low heat.

With reference to the patent literature, a sterilization technique was disclosed in U.S. Pat. No. 5,786,598 to Clark et al., entitled "Sterilization of Packages and Their Contents Using High-Intensity, Short-Duration Pulses of Incoherent, Polychromatic Light in a Broad Spectrum." As noted in the title, the Clark '598 patent involves the use of high-intensity, short-duration pulses of incoherent, polychromatic light in a broad spectrum to sterilize product containers and deactivate microorganisms therein. The Clark '598 patent proposes "the deactivation of microorganisms within parenteral and/or enteral solutions and packages or within contact lens solutions and packages and/or ophthalmic solutions and packages." [See col. 1, lines 11-20]. The use of short-duration pulses of incoherent, polychromatic light in a broad spectrum, as disclosed in the Clark '598 patent, is believed to be ineffective and/or unacceptable for at least some aspects of the proposed applications.

Despite efforts to date, a need remains for cost-effective, efficient systems and methods for sterilization of container systems and/or container-packaged products (e.g., liquid and/or solid products/solutions and/or packaging/container systems for liquid and/or solid products/solutions), wherein such sterilization regimen achieves a desired sterilization level without negatively affecting the physical properties of the package/container systems and/or the efficacy of the underlying products/systems. These and other inefficiencies and opportunities for improvement are addressed and/or overcome by the systems and methods of the present disclosure.

SUMMARY

The present disclosure provides for advantageous methods, systems and apparatus for UV light sterilization of container systems and/or container-packaged products, and, more particularly, to methods, systems and apparatus for monochromatic UV light sterilization of liquid and/or solid products/solutions and/or packaging/container systems for liquid and/or solid products/solutions. For example, the disclosed systems and methods may be used for sterilization of beverage and/or food products and/or their containers, medicines and/or their containers, pharmaceuticals and/or their containers, vitamins and/or their containers, infusion products and/or their containers, clinical and/or non-clinical solutions/systems and/or their containers, enteral and/or parenteral solutions/systems and/or their containers, and the like.

In general, monochromatic UV light sterilization is an advantageous, non-chemical/non-thermal alternative sterilization technique to terminal sterilization and aseptic processing. For example, monochromatic sterilization provides a means to sterilize heat sensitive products in lieu of aseptic processing. One benefit of monochromatic sterilization is that the sterilization may occur in-line, e.g., immediately downstream of the filling operation, resulting in reduced non-sterile hold times. In general, monochromatic UV light sterilization is also easier on the container/closure system and allows for the use of alternate/low temperature container systems and materials. Further, monochromatic sterilization provides a significant reduction of energy costs and waste generation over conventional steam sterilization.

In exemplary embodiments, the present disclosure provides for improved systems and methods for the sterilization of container systems and/or container-packaged products using monochromatic, continuous wave, high-intensity, incoherent light in multiple light source configurations, wherein such sterilization regimen achieves a desired sterilization level without negatively affecting the physical properties of the package/container systems and/or the efficacy of the underlying products/systems. In one embodiment, the sterilization is achieved by using monochromatic, continuous wave, high-intensity, incoherent light in at least two light source configurations.

The present disclosure provides for a sterilization system including at least one container system having a container material and a product contained in the container material; a treatment zone having at least a first light source and a second light source, each light source having a light device housed in a housing, with each light device configured and dimensioned to generate and transmit substantially ambient temperature and substantially monochromatic light into the treatment zone; a transport system having at least one securing means for releasably securing at least one container system to the transport system, the at least one securing means configured and dimensioned to position the at least one container system to establish a product treatment area of product having substantially no air bubbles in the product treatment area; wherein the transport system is configured and dimensioned to transport the at least one container system to or through the treatment zone; and wherein the at least one container system receives monochromatic light energy from each light source while in the treatment zone to achieve a sterilization effect of the at least one container system.

The present disclosure also provides for a sterilization system wherein the at least one container system is a parenteral pharmaceutical product container system; and wherein the product is a parenteral pharmaceutical product or solution. The present disclosure also provides for a sterilization system wherein the at least one container system is an intravenous bag that is configured and dimensioned to contain from about 5 ml of product or solution to about 5000 ml of product or solution. The present disclosure also provides for a sterilization system wherein the container material is selected from the group consisting of polyethylene (PE), polypropylene (PP), polyolefins and combinations thereof.

The present disclosure also provides for a sterilization system wherein the monochromatic light is generated at a wavelength that is substantially at a wavelength selected from the group consisting of 193 nm, 207 nm, 222 nm, 248 nm, 254 nm, 282 nm, 308 nm, 354 nm and 361 nm. The present disclosure also provides for a sterilization system wherein the treatment zone is an exposure tunnel having a cover or cover frame. The present disclosure also provides for a sterilization system wherein at least a portion of the interior surface of the cover or cover frame is coated or partially coated with at least one reflective material. The present disclosure also provides for a sterilization system wherein the at least one securing means releasably secures at least one port of at least one container system to the transport system. The present disclosure also provides for a sterilization system wherein the at least one securing means further positions the at least one container system in a substantially vertical position. The present disclosure also provides for a sterilization system wherein the at least one securing means is configured and dimensioned to minimize or eliminate the shadowing effects from the at least one securing means on the at least one container system.

The present disclosure also provides for a sterilization system wherein the transport system is incorporated in-line and downstream of a container system filling process, and wherein the transport rate of the at least one container system to or through the treatment zone is substantially equal to the filling rate of the container system filling process. The present disclosure also provides for a sterilization system wherein the sterilization effect of the at least one container system is achieved without negatively affecting the physical properties of the container system or the efficacy of the product contained in the container material. The present disclosure also provides for a sterilization system wherein the first light source is positioned on one side of the transport system and the second light source is positioned on the other side of the transport system to provide light energy to substantially every surface of the at least one container system while in the treatment zone.

The present disclosure also provides for a sterilization system further including a third, fourth, fifth and sixth light source, each light source configured and dimensioned to generate and transmit substantially ambient temperature and substantially monochromatic light into the treatment zone; and wherein the first, third and fifth light sources are positioned on one side of the transport system and the second, fourth and sixth light source are positioned on the other side of the transport system to provide light energy to substantially every surface of the at least one container system while in the treatment zone. The present disclosure also provides for a sterilization system wherein each light source is further configured and dimensioned to move vertically up or down relative to the central axis of the treatment zone to achieve the sterilization effect of the at least one container system.

The present disclosure also provides for a sterilization system wherein at least one light source is moved vertically up or down relative to the central axis of the treatment zone based upon at least one variable of the at least one container system. The present disclosure also provides for a sterilization system wherein the at least one variable of the at least one container system is selected from the group consisting of container size, fill volume, type of product contained in the container system, color of the container system or product, spacing of the container system or systems entering the treatment zone, label copy, amount of printed material or ink on the container system and reflectance value.

The present disclosure also provides for a sterilization system wherein each light source is further configured and dimensioned to move closer to or farther away from the central axis of the treatment zone to achieve the sterilization effect of the at least one container system. The present disclosure also provides for a sterilization system wherein at least one light source is moved closer to or farther away from the central axis of the treatment zone based upon at least one variable of the at least one container system. The present disclosure also provides for a sterilization system wherein the at least one variable of the at least one container system is selected from the group consisting of container size, fill volume, type of product contained in the container system, color of the container system or product, spacing of the container system or systems entering the treatment zone, label copy, amount of printed material or ink on the container system and reflectance value.

The present disclosure also provides for a sterilization system wherein the light device is an excimer light device.

The present disclosure also provides for a sterilization system including at least one container system; a treatment zone having at least a first light source and a second light source, each light source having a light device housed in a housing, with each light device configured and dimensioned to generate and transmit substantially ambient temperature and substantially monochromatic light into the treatment zone; a transport system configured and dimensioned to transport the at least one container system to or through the treatment zone; wherein the at least one container system receives monochromatic light energy from each light source while in the treatment zone to achieve a sterilization effect of the at least one container system; wherein each housing includes two side walls and a back wall, at least one of the side walls sloping inwardly at an angle to meet the back wall; and wherein the at least one inwardly sloping side wall includes at least one reflector panel releasably secured to the inwardly sloping side wall, the at least one reflector panel configured and dimensioned to provide for the delivery or accentuation of light energy from the light source to the at least one container system while in the treatment zone.

The present disclosure also provides for a sterilization system wherein the at least one container system is a parenteral pharmaceutical product container system. The present disclosure also provides for a sterilization system wherein the at least one container system is fabricated from material selected from the group consisting of polyethylene (PE), polypropylene (PP), polyolefins and combinations thereof.

The present disclosure also provides for a sterilization system wherein the back wall is a substantially straight back wall; and wherein the at least one inwardly sloping side wall slopes inwardly at about a 45° angle with respect to the plane of the substantially straight back wall. The present disclosure also provides for a sterilization system wherein the at least one inwardly sloping side wall slopes inwardly at about a 45° angle with respect to the central axis of the light device. The present disclosure also provides for a sterilization system wherein both side walls slope inwardly at an angle to meet the back wall. The present disclosure also provides for a sterilization system wherein each side wall and the back wall each include at least one releasably secured reflector panel. The present disclosure also provides for a sterilization system wherein the at least one inwardly sloping side wall meets the back wall with the at least one reflector panel spaced a distance away from the closest surface of the light device.

The present disclosure also provides for a sterilization system wherein the at least one reflector panel is coated or partially coated with at least one reflective material. The present disclosure also provides for a sterilization system wherein the at least one reflective material is substantially matched to the monochromatic wavelength generated and transmitted by the light source. The present disclosure also provides for a sterilization system wherein the at least one reflector panel is at about a 96% reflectance level for a selected monochromatic wavelength.

The present disclosure also provides for a method for controlling a light source including measuring the amount of printed material on at least one container system with a measuring device; generating a control signal based upon the measured amount of printed material; sending the control signal to at least one light source that generates and transmits substantially ambient temperature and substantially monochromatic light; wherein the control signal establishes or changes at least one operating parameter of the at least one light source.

The present disclosure also provides for a method for controlling a light source wherein the at least one container system is a parenteral pharmaceutical product container system. The present disclosure also provides for a method for controlling a light source wherein the printed material includes ink. The present disclosure also provides for a method for controlling a light source wherein the measuring device includes a reflectance measuring unit or reflectometer. The present disclosure also provides for a method for controlling a light source wherein the measuring device measures the reflectance of the at least one container system to generate the control signal. The present disclosure also provides for a method for controlling a light source wherein the at least one operating parameter of the at least one light source is UV intensity, UV wavelength, or power output.

Additional advantageous features, functions and applications of the disclosed systems and methods of the present disclosure will be apparent from the description which follows, particularly when read in conjunction with the appended figures.

BRIEF DESCRIPTION OF THE DRAWINGS

To assist those of ordinary skill in the art in making and using the disclosed systems and methods, reference is made to the appended figures, wherein.

DETAILED DESCRIPTION

Figure 1:
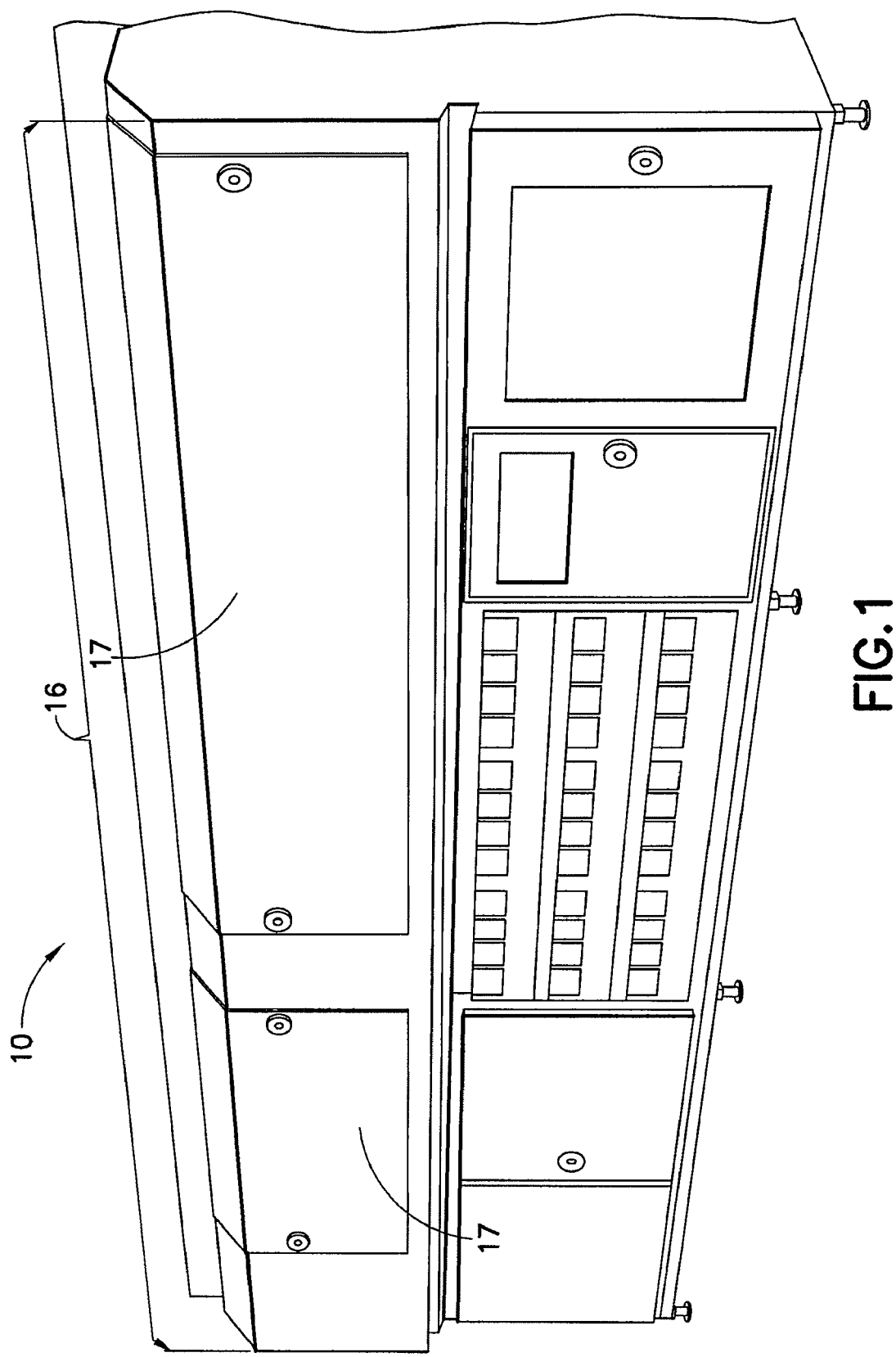
FIG. 1 is a perspective view of an embodiment of a sterilization system according to the present disclosure.

The present disclosure provides for methods, systems and apparatus for UV light sterilization of container systems and/or container-packaged products. More particularly, the present disclosure provides for improved methods, systems and apparatus for monochromatic UV light sterilization of liquid and/or solid products/solutions and/or packaging/container systems for liquid and/or solid products/solutions. In exemplary embodiments, the present disclosure provides for improved methods, systems and apparatus for monochromatic UV light sterilization of beverage and/or food products and/or their containers, medicines and/or their containers, pharmaceuticals and/or their containers, vitamins and/or their containers, infusion products and/or their containers, clinical and/or non-clinical solutions/systems and/or their containers, enteral and/or parenteral solutions/systems and/or their containers, and the like.

In one embodiment, the present disclosure provides for improved methods, systems and apparatus for monochromatic UV light sterilization of parenteral pharmaceutical products/solutions and/or packaging/container systems for parenteral pharmaceutical products/solutions and the like. As used herein, a "parenteral pharmaceutical product" is a pharmaceutical product (including the container/packaging system and/or materials that house and/or contain the pharmaceutical product), whether for human or animal use, taken into the body or administered in an intravenous or injectable manner. For example, a "parenteral pharmaceutical product" includes, without limitation, injectable products, intravenous products, water for injection, intravenous or injectable nutritional products, irrigation solutions, or the like.

In exemplary embodiments, the present disclosure provides for improved systems and methods for the sterilization of container systems and/or container-packaged products (e.g., liquid and/or solid products/solutions and/or packaging/container systems for liquid and/or solid products/solutions) using monochromatic, continuous wave, high-intensity, incoherent light in multiple light source configurations, wherein such sterilization regimen achieves a desired sterilization level without negatively affecting the physical properties of the package/container systems and/or the efficacy of the underlying products/systems. As such, the disclosed sterilization systems and methods advantageously preserve physical and performance properties of the products/systems while achieving a desired level of sterilization. The present disclosure provides an advantageous approach to the sterilization of container systems and/or container packaged products, including containers/products that include heat sensitive materials. According to exemplary embodiments of the present disclosure, the disclosed sterilization systems and methods are effective in inactivating viral and bacterial microorganisms without physical or performance-related damage to the treated containers/products.

More specifically, at least two light sources may be employed according to the present disclosure to deliver monochromatic germicidal light at radiance levels of about 200 mW/cm$^2$ to 600 mW/cm$^2$ to deactivate multiple organisms. In one embodiment, the sterilization is achieved by using monochromatic, continuous wave, high-intensity, incoherent light in multiple light source configurations. Unlike steam sterilization processes, monochromatic UV light sterilization operates at ambient temperatures. For example, the germicidal light of the present disclosure is advantageously delivered at a substantially ambient temperature so as to avoid potential temperature-related damage to the packaging/container system. According to exemplary embodiments of the present disclosure, the germicidal light may be generated and delivered at substantially discrete wavelengths, e.g., wavelengths of 193 nm; 207 nm; 222 nm; 248 nm; 254 nm; 282 nm; 308 nm; 354 nm and 361 nm. The light wavelength may be advantageously controlled to +/−5 nm. For example, the monochromatic UV light wavelength may be controlled to a selectable bandwidth to optimize container/packaging system penetration and microbial kill. In exemplary embodiments of the present disclosure, containers/products are sterilized to Sterilization Assurance Levels of at least $10^{-5}$ cfu/ml (colony forming units/ml).

The disclosed wavelengths are generally effective for use in sterilizing a range of materials (e.g., packaging/container materials), including, without limitation, polyethylene (PE), polypropylene (PP), polyolefins, etc. Additionally, the disclosed wavelengths are generally effective for use in sterilizing products/solutions contained within container/packaging systems (e.g., microorganisms located within container-packaged parenteral products/solutions). In exemplary embodiments, microbial inactivation by UV light occurs from nucleotide damage following UV absorption which prevents the replication of the microorganism. For example, damage may result in the formation of pyrimidine dimers due to the covalent bonds between adjacent pyrimidines on the same RNA or DNA strand.

Current practice provides that some packaging/container system materials and/or products cannot endure the extremes of heat and/or pressure generated during steam sterilization. Current practice also provides that general steam sterilization techniques are not readily incorporated into an in-line (i.e., continuous or substantially continuous) process, such as, for example, a packaging/container system filling process. In exemplary embodiments, the present disclosure provides for improved systems/methods for the UV light sterilization of container systems and/or container-packaged products wherein such sterilization regimen achieves a desired sterilization level without negatively affecting the physical properties of the package/container systems and/or the efficacy of the underlying products/systems while also allowing for the use of alternate and/or low temperature package/container systems and/or materials, thereby providing a significant manufacturing and commercial advantage as a result. The present disclosure also provides for improved systems/methods for the UV light sterilization of container systems and/or container-packaged products where the sterilization treatment is readily incorporated into an in-line (i.e., continuous or substantially continuous) process (e.g., immediately downstream of the filling process/operation) in which the sterilization may be accomplished in a matter of seconds, thereby reducing non-sterile hold times and providing a significant manufacturing and commercial advantage as a result. In addition, the UV light sterilization systems and methods of the present disclosure provide a significant reduction of energy costs and waste generation over conventional steam sterilization, thereby reducing the cost of manufacture and providing a significant commercial advantage as a result.

The sterilization systems and methods of the present disclosure may be operated/performed in a batch, semi-batch or continuous mode. In an exemplary embodiment of the present disclosure, container systems and/or container packaged products (e.g., parenteral pharmaceutical products/solutions and/or packaging/container systems for parenteral pharmaceutical products/solutions) are treated continuously or semi-continuously by positioning the container systems/products on a moving conveyor/transport system or the like, such that the container systems/products are moved to and/or through a treatment zone or exposure tunnel. The conveyor/transport system may take the form of conveyor belt system, although the present disclosure is not limited thereto.

In exemplary embodiments, the sterilization systems and methods of the present disclosure include a treatment zone or exposure tunnel, wherein the treatment zone or exposure tunnel includes at least two UV light sources that are adapted to deliver monochromatic UV light to each container system/product which moves into/through the treatment zone/exposure tunnel. While in the treatment zone or exposure tunnel, a desired monochromatic UV light dose may then be delivered to each container system/product to achieve a sterilization effect. For example, a desired monochromatic light dose may be delivered to each container system and/or into the product/solution contained in each container system to achieve a sterilization effect of each container system/product.

In exemplary embodiments, the speed at which the container systems/products are moved to and/or through the treatment zone/exposure tunnel may be adjusted so as to achieve the desired energy treatment level, e.g., based on a desired residence time of each container system/product within the treatment zone/exposure tunnel. Typically, process parameters (e.g., UV wavelength, UV intensity, etc.) may be controlled/modified so as to affect a desired sterilization result according to the present disclosure, and such processing parameters may be adjusted/selected (either alone or in combination with the rate/residence time of the container systems/products within the treatment zone/exposure tunnel) to achieve desired sterilization results.

For example, the intensity of the light sources utilized in the treatment zone/exposure tunnel may be adjusted to achieve desired sterilization results. In exemplary embodiments, the UV intensity of each light source may be monitored and/or controlled to maintain a desired UV dosage. In addition, exposure conditions (e.g., conveyor speed, UV wavelength, UV intensity, etc.) can be specific for each container system/product grouping. Furthermore, the UV light sources may be advantageously moved and/or spaced in the treatment zone/exposure tunnel in accordance with the various shapes, sizes and/or spacing of the container systems/products entering the treatment zone/exposure tunnel (e.g., based on the container size, fill volume, product, color, spacing, etc.). Each UV light source may be operated at the same or different energy intensities to achieve desired sterilization results, whether based upon or independent of container system/product variables (e.g., container size, shape, color, material, product, fill-volume, label copy, spacing, etc.).

According to exemplary embodiments of the present disclosure, a control system may be in communication with each light source to control the light source operating parameters. In one embodiment, the control system includes a processor that is programmed to operate the light sources at desired intensity levels and/or time periods. In general, the UV intensity is monitored and controlled to maintain the desired UV dosage. In exemplary embodiments, each light source includes at least one sensor to monitor wavelength and to monitor/control intensity. For example, each light source may include three sensors to monitor wavelength and to monitor/control intensity. In exemplary embodiments, the at least one light source sensor is linked to the control system. The control system may also be linked to the conveyor/transport system to control/maintain the speed of the containers/products moving to and/through the treatment zone/exposure tunnel. For example, the conveyor/transport system may be maintained at a constant speed, or the conveyor/transport system may operate at variable speeds.

In exemplary embodiments, a defined UV intensity range may be established for each container/product grouping (e.g., container size, fill-volume, etc.). The control system may automatically adjust the power to each UV light source to maintain each defined UV intensity range for each container/product grouping. The treatment parameters (e.g., UV intensity range) are generally selected based on the treatment for a single organism, or for multiple organisms. Typical organisms may include, without limitation, *Bacillus pumilus* (spore former), *Candida albican* (yeast), lipid and non-lipid virus, *Clostridium sporogenes* (anaerobic spore former), *Alicyclobacillus, Staphylococcus aureus* (vegetative Gram positive), *Pseudomonas aeruginosa* (vegetative Gram negative), *Aspergillus niger* (filamentous fungi), *Mycobacterium terrae*, Porcine Parvo Virus (PPV and B19), *Lysteria, Salmonella, B. atrophaeus, M. luteus* and *S. maltophilia*. In exemplary embodiments, containers/products which are underdosed or overdosed will be automatically ejected/rejected, and containers/products meeting the defined dose requirements will be automatically etched (e.g., laser etched) to indicate sterilization has been affected, in lieu of chemical indicators used with traditional steam sterilization processes. The systems and methods of the present disclosure are effective in treating container systems/products of varying sizes, shapes and geometries.

In the description which follows, like parts are marked throughout the specification and drawings with the same reference numerals, respectively. Drawing figures are not necessarily to scale and in certain views, parts may have been exaggerated for purposes of clarity.

Figure 2:
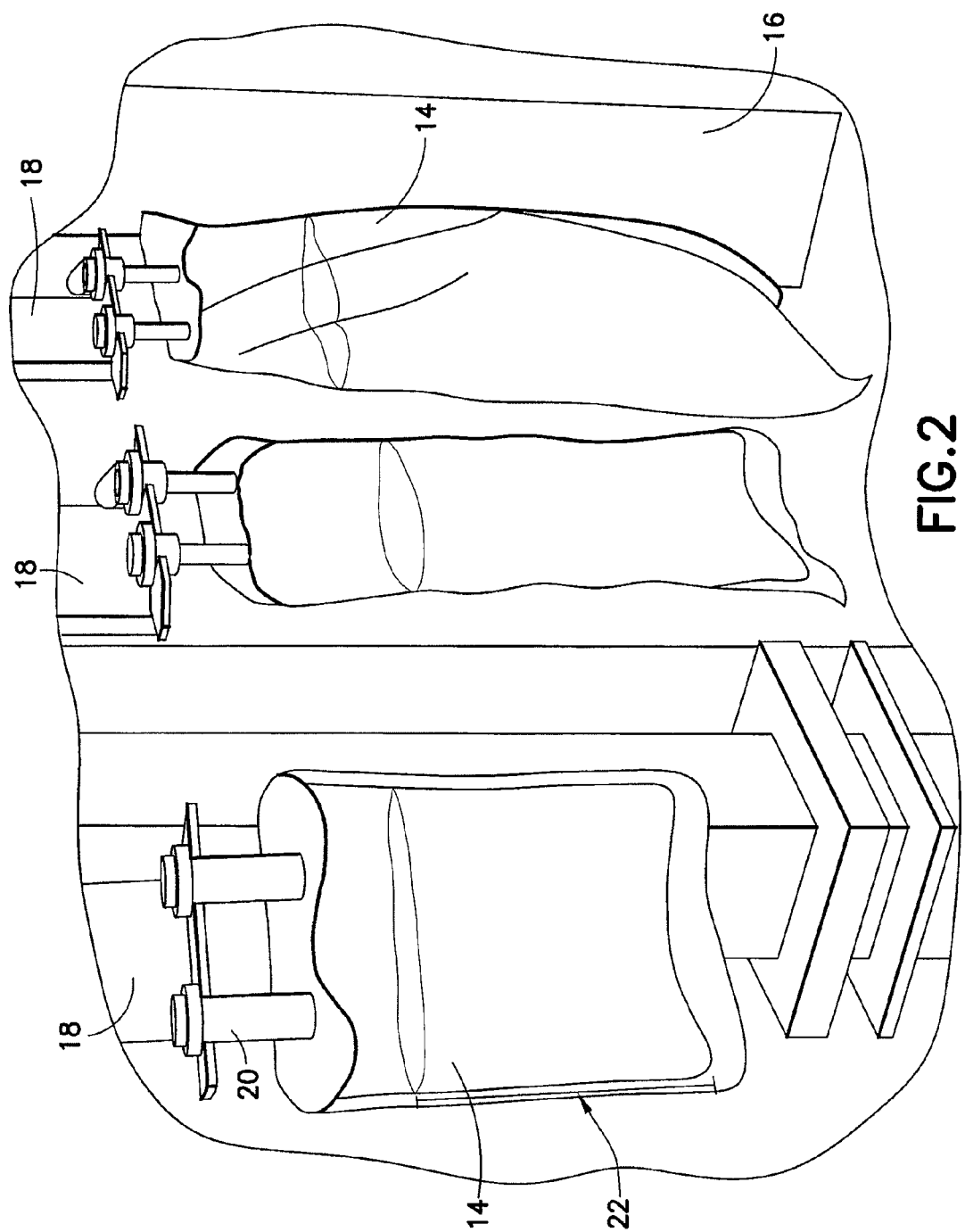
FIG. 2 is a partial view of a sterilization system according to the present disclosure.
Figure 3:
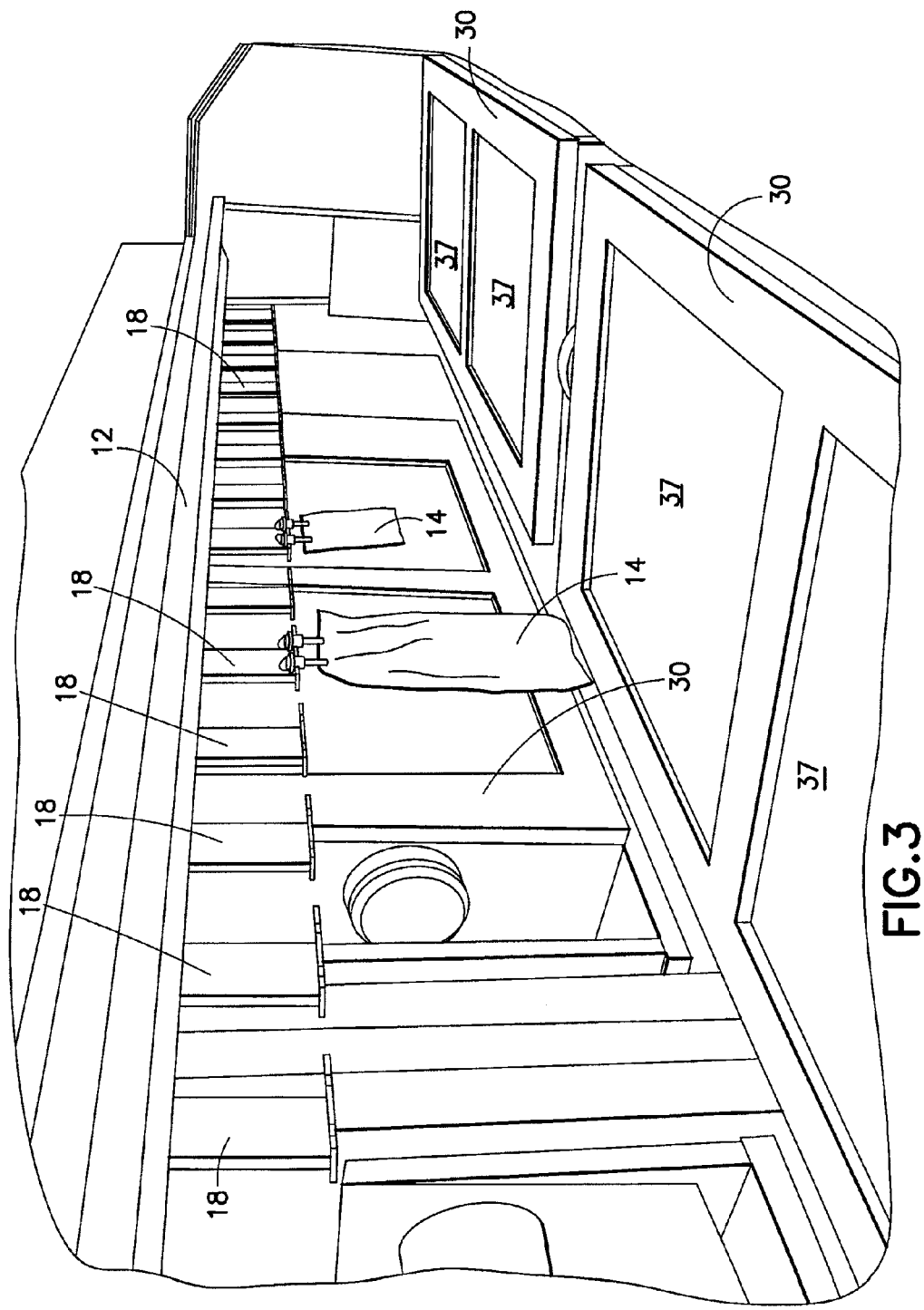
FIG. 3 is a partial view of a sterilization system according to the present disclosure.

Referring now to the drawings, and in particular to FIG. 1, there is illustrated a sterilization system 10 depicting an embodiment of the present disclosure. In one embodiment, sterilization system 10 is a monochromatic UV light sterilization system that is configured and dimensioned for UV light sterilization of container systems and/or container-packaged products 14, wherein such sterilization regimen achieves a desired sterilization level without negatively affecting the physical properties of the package/container systems 14 and/or the efficacy of the underlying products/systems 14 (FIGS. 2 and 3). In an exemplary embodiment, sterilization system 10 is a monochromatic UV light sterilization system that is configured and dimensioned for UV light sterilization of parenteral pharmaceutical products/solutions and/or packaging container systems for parenteral pharmaceutical products/solutions.

In exemplary embodiments and as shown in FIG. 1, sterilization system 10 is a mono-block assembly about 15' long, about 3' wide, and about 5' high. Typically, sterilization system 10 includes a conveyor/transport system 12. In exemplary embodiments and as shown in FIGS. 1-3, conveyor/transport system 12 is configured and dimensioned to transport at least one container system/product 14 (FIGS. 2 and 3) to and/or through a treatment zone 16 of sterilization system 10.

In one embodiment, treatment zone 16 is an exposure tunnel that further includes a cover and/or cover frame 17. The cover and/or cover frame 17 of treatment zone 16 is typically fabricated from a material that is effective in filtering/shielding the UV light rays produced by the sterilization system 10 so as to protect operators, etc. In general, the size and geometry of the cover and/or cover frame 17 is typically selected so as to treat the container systems/products 14 in the treatment zone 16, while ensuring that the emitted light rays are filtered/shielded from operators. In exemplary embodiments of the present disclosure, at least a portion of the interior surface (e.g., the surface facing the container systems/products 14 in the treatment zone 16) of the cover and/or cover frame 17 may be coated, partially coated and/or multiply coated with at least one reflective material, such as, for example, a monochromatic wavelength specific dielectric coating and/or material. Examples of suitable monochromatic wavelength specific dielectric coatings and/or materials include, without limitation, silicon dioxide, hafnium dioxide and the like. In an exemplary embodiment, at least a portion of the interior surface of the cover and/or cover frame 17 of treatment zone 16 is coated with at least one reflective material (e.g., a monochromatic wavelength specific dielectric coating and/or material). In one embodiment, the entire interior surface of the cover and/or cover frame 17 of treatment zone 16 is coated with at least one reflective material. In an alternative embodiment, the interior surface of the cover and/or cover frame 17 of treatment zone 16 is not coated with any reflective material(s).

Exemplary conveyor/transport system 12 may take the form of conveyor system (e.g., conveyor belt system), although the present disclosure is not limited thereto. Rather, the conveyor/transport system 12 may take a variety of forms, including without limitation, rotating indexed machinery and/or tracks of various configurations. The conveyor/transport system 12 may be operated in a batch, semi-batch or continuous mode. In exemplary embodiments, the speed(s) at which the container systems/products 14 are moved to and/or through the treatment zone 16 may be adjusted so as to achieve the desired energy treatment level based on a desired residence time (i.e., exposure time) of each container system/product 14 within the treatment zone 16. For example, the conveyor/transport system 12 may be maintained at a constant speed, or the conveyor/transport system 12 may be operated at variable speeds.

Exemplary at least one container system/product 14 takes the form of a parenteral pharmaceutical product/solution and/or a packaging container system for a parenteral pharmaceutical product/solution, although the present disclosure is not limited thereto. Rather, container system/product 14 may take a variety of forms. For example, the disclosed systems and methods may be used for sterilization of beverage and/or food products and/or their containers, medicines and/or their containers, pharmaceuticals and/or their containers, vitamins and/or their containers, infusion products and/or their containers, clinical and/or non-clinical solutions/systems and/or their containers, enteral and/or parenteral solutions/systems and/or their containers, and the like.

In exemplary embodiments, the at least one container system/product 14 may be fabricated from a variety of materials, including, without limitation, polyethylene (PE), polypropylene (PP), polyolefins and the like. In one embodiment, the at least one container system/product 14 is fabricated from polyethylene (PE), polypropylene (PP) and/or polyolefins, and the at least one container system/product 14 may include a product/solution, such as, for example, a parenteral product/solution.

In an exemplary embodiment of the present disclosure, the at least one container system/product 14 is a bag, such as, for example, an intravenous (IV) bag. The IV bag 14 may contain a product/solution, such as, for example, a parenteral product/solution. For example, the container system/product 14 may be configured and dimensioned to house and/or contain from about 5 ml of product/solution to about 5000 ml of product/solution, although the present disclosure is not limited thereto. In exemplary embodiments of the present disclosure, the container system/product 14 may be configured and dimensioned to house and/or contain from about 50 ml of product/solution to about 1000 ml of product/solution.

Typically, conveyor/transport system 12 includes at least one securing means or holder 18 (FIG. 2) that is configured and dimensioned to releasably secure each container system/product 14 to the conveyor/transport system 12 of sterilization system 10. For example, the container system/product 14 may include at least one port 20 (e.g., at least one filling and/or closure port 20 at the top of each container system/product 14), and each securing means or holder 18 may be configured and dimensioned to releasably secure each container system/product 14 to the conveyor/transport system 12 by releasably securing/holding the at least one port 20 of container system/product 14. In an exemplary embodiment, the at least one securing means or holder 18 is fabricated from series 300 stainless steel, although the present disclosure is not limited thereto. Rather, securing means or holder 18 may take a variety of forms. In one embodiment, the at least one securing means or holder 18 is configured and dimensioned to have about a 10-degree pitch or the like (e.g., a 10-degree pitch fixed relative to the ground) in order to ensure that each container system/product 14 is releasably secured to the conveyor/transport system 12. In exemplary embodiments and as depicted in FIG. 2, the at least one securing means or holder 18 is configured and dimensioned to position a container system/product 14 to establish a product/solution treatment area 22 of product/solution having substantially no air bubbles in the product solution treatment area 22.

Figure 7:
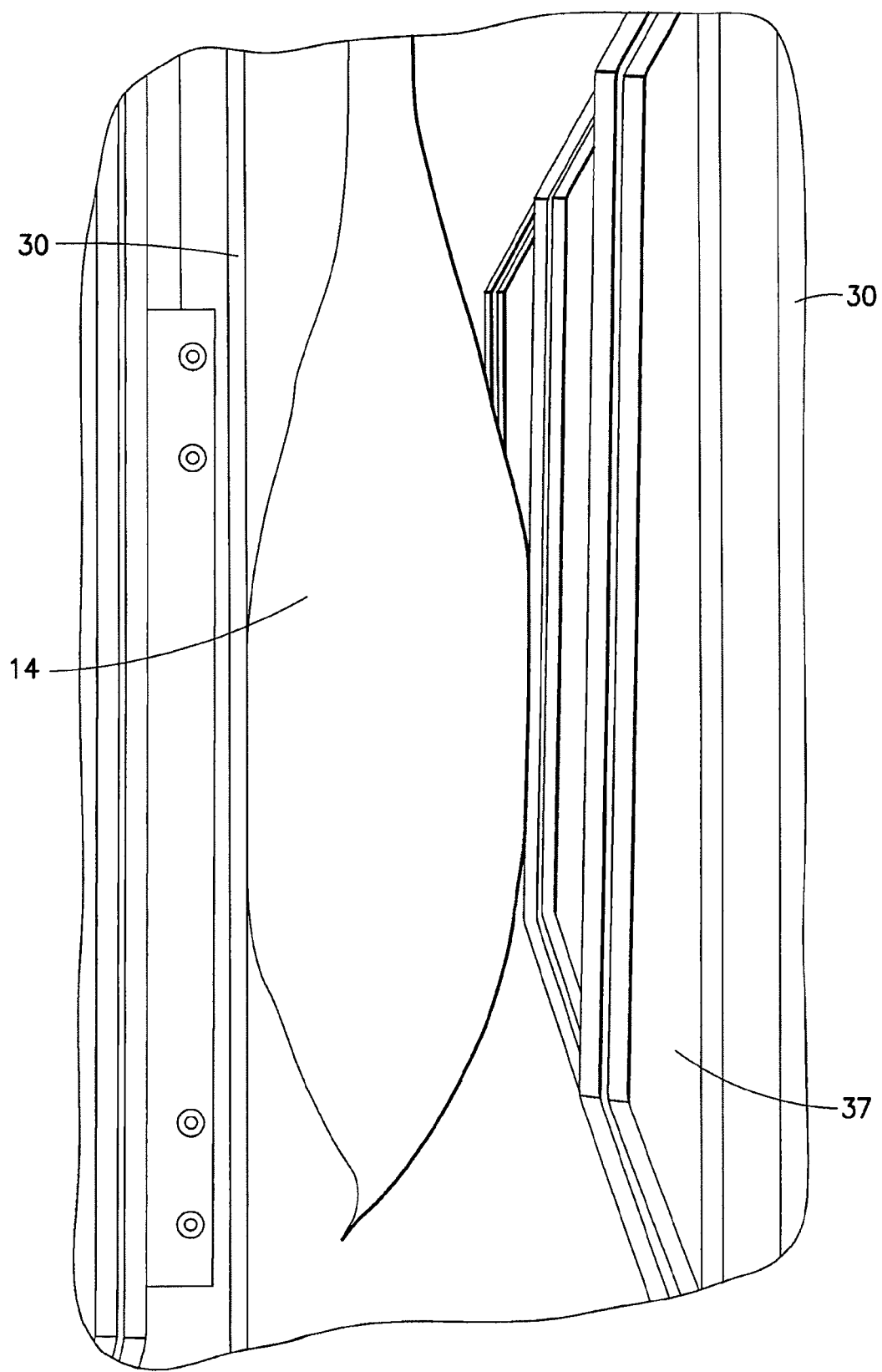
FIG. 7 is a partial view of a sterilization system according to the present disclosure.

In one embodiment, each container system/product 14 is in a vertical or substantially vertical position (FIGS. 2, 3 and 7) prior to entering the treatment zone 16, so that any product/solution 14 contained and/or housed in the container system/product 14 contains substantially no air bubbles within the product/solution treatment area 22. For example, each securing means or holder 18 may be configured and dimensioned to releasably secure each container system/product 14 so that each container system/product 14 is maintained in a vertical or substantially vertical position for the entire time that each container system/product 14 is in (e.g., passes through) the treatment zone 16. In general, this ensures that any product/solution contained and/or housed in each container system/product 14 contains substantially no air bubbles within the product/solution treatment area 22, while each container system/product 14 is in the treatment zone 16. In addition, each securing means or holder 18 may be configured and dimensioned to minimize/eliminate the shadowing effect(s) on each container system/product 14 while each container system/product is in the treatment zone 16 (e.g., a shadowing effect of the securing means or holder 18 on the container system/product 14), thereby providing for the maximum array of UV light to substantially every surface of each container system/product 14 while in the treatment zone 16. In exemplary embodiments, each portion/area/surface of each container system/product 14 is treated with UV light while in the treatment zone 16.

The conveyor/transport system 12 may be readily incorporated into an in-line (e.g., a continuous or semi-continuous) process. For example, the conveyor/transport system 12 may be incorporated in-line, immediately downstream of a container system/product 14 filling process/operation, wherein the conveyor/transport system 12 may deliver the recently filled container system(s)/product(s) 14 to and/or through the treatment zone 16 immediately after filling, so that sterilization may be accomplished in a matter of seconds, for example, thereby reducing non-sterile hold-times of the container system(s)/product(s) 14. In exemplary embodiments, the conveyor/transport system 12 is adapted to transport the container systems/products 14 to and/or through the treatment zone 16 at a rate from about ten container systems/products 14 per minute, to a rate of about eighty container systems/products 14 per minute. The conveyor/transport system 12 may be adapted to transport the container systems/products 14 to and/or through the treatment zone 16 at a rate from about sixty-eight container systems/products 14 per minute, to a rate of about seventy-five container systems/products 14 per minute. In exemplary embodiments, the delivery rate of the container systems/products 14 to and/or through the treatment zone 16 is substantially equal to the rate of the container system/product 14 filling process (e.g., from about sixty-eight container systems/products 14 per minute, to about seventy-five container systems/products 14 per minute).

In exemplary embodiments and as shown in FIGS. 1, 3, 4, 4A and 6, treatment zone 16 includes at least two monochromatic UV light sources 30 that are adapted to generate and transmit substantially monochromatic UV light to each container system/product 14 which moves into/through the treatment zone 16 to achieve a sterilization effect. In exemplary embodiments, the present disclosure provides for improved systems and methods for the sterilization of container systems/products 14 using monochromatic, continuous wave, high-intensity, incoherent light in multiple light source 30 configurations, wherein such sterilization regimen achieves a desired sterilization level without negatively affecting the physical properties of the container systems/products 14 and/or the efficacy of the underlying products/systems. In exemplary embodiments, each light source 30 may emit UV light over a large active area, and each light source 30 is configured and dimensioned to operate at substantially ambient temperatures.

In general, monochromatic UV light sterilization is an advantageous, non-chemical/non-thermal alternative sterilization technique to terminal sterilization and aseptic processing. For example, monochromatic sterilization provides a means to sterilize heat sensitive products in lieu of aseptic processing. One benefit of monochromatic sterilization is that the sterilization may occur in-line, e.g., immediately downstream of the filling operation, resulting in reduced non-sterile hold times. In general, monochromatic UV light sterilization is also easier on the container/closure system and allows for the use of alternate/low temperature container systems and materials. Further, monochromatic sterilization provides a significant reduction of energy costs and waste generation over conventional steam sterilization. According to exemplary embodiments of the present disclosure, the disclosed sterilization systems and methods are effective in inactivating viral and bacterial microorganisms without physical or performance-related damage to the treated containers/products 14.

In exemplary embodiments, treatment zone 16 includes at least two monochromatic UV light sources 30 that are adapted to deliver monochromatic UV light to each container system/product 14 which moves into/through the treatment zone 16, and wherein each light source 30 is positioned on each side of the conveyor/transport system 12 to provide UV light to substantially every surface of each container system/product 14 while in the treatment zone 16 to achieve a sterilization effect. In one embodiment, each light source 30 provides substantially uniform UV light intensity to substantially every surface of each container system/product 14 while in the treatment zone 16 to achieve a sterilization effect. Alternatively, each light source 30 may provides variable UV light intensity to substantially every surface of each container system/product 14 while in the treatment zone 16 to achieve a sterilization effect. In an exemplary embodiment of the present disclosure, treatment zone 16 includes six monochromatic UV light sources 30 that are adapted to deliver monochromatic UV light to each container system/product 14 which moves into/through the treatment zone 16, whereby three light sources 30 are positioned on each side of the conveyor/transport system 12 to provide UV light to substantially every surface of each container system/product 14 while in the treatment zone 16 to achieve a sterilization effect. For example, a desired monochromatic UV light dose may be delivered to each container system/product 14 and/or into the product/solution contained in each container system/product 14 to achieve a sterilization effect of each container system/product 14.

In exemplary embodiments, each UV light source 30 may be advantageously moved and/or spaced in the treatment zone 16 in accordance with the various shapes, sizes and/or spacing of the container systems/products 14 entering the treatment zone 16. For example, each light source 30 may be moved vertically (e.g., up or down) relative to the central axis of treatment zone 16, horizontally (e.g., left or right) parallel to the central axis of treatment zone 16, and/or closer or farther away from each container system/product 14 (e.g., closer to or farther away from the central axis of the treatment zone) to achieve the desired sterilization effect of each container system/product 14 passing through the treatment zone 16 based upon, for example, container system/product 14 factors including, without limitation, container 14 size, fill volume of the containers 14, type of product/solution contained in the container system/product 14, color of the container system/product 14, spacing of the container systems/products 14 entering the treatment zone 16, label copy of the container systems/products 14, amount of ink on the container/packaging material 14 and/or container 14 reflectance values, etc. Each light source 30 may be moved and/or spaced in the treatment zone 16 by machinery/mechanisms/structures associated with the sterilization system 10, or each light source 30 may be moved manually by operators, etc. In addition, each UV light source 30 may be operated at the same or different energy intensities to achieve desired sterilization results, whether based upon or independent of container system/product 14 variables (e.g., container size, shape, color, material, product, fill-volume, label copy, spacing, etc.). Moreover, each container system/product 14 entering/passing through the treatment zone 16 may be positioned in a static position (e.g., in a substantially vertical position) relative to each light source 30, or each container system/product may be moved (e.g., up/down, left/right) or rotated while entering/passing through the treatment zone 16 to achieve the desired sterilization effect.

In exemplary embodiments, each light source 30 may deliver monochromatic germicidal light to each container system/product 14 at radiance levels of about 200 mW/cm$^2$ to 600 mW/cm$^2$ to deactivate multiple organisms. In general, the germicidal light may be generated and delivered at substantially discrete wavelengths, e.g., wavelengths of 193 nm; 207 nm; 222 nm; 248 nm; 254 nm; 282 nm; 308 nm; 354 nm and 361 nm. The light wavelength may be controlled to +/−5 nm. For example, the monochromatic UV light wavelength may be controlled to a selectable bandwidth to optimize container system/product 14 penetration and microbial kill. In exemplary embodiments of the present disclosure, containers systems/products 14 are sterilized to Sterilization Assurance Levels of at least 10$^{-5}$ cfu/ml.

As shown in FIGS. 4, 4A, 5 and 5A, an exemplary light source 30 includes light device 32 housed in housing 34 for the generation, transmission and/or delivery of ambient temperature, monochromatic germicidal UV light through at least one window 37. In exemplary embodiments, housing 34 is a metal housing or metal reactor, and the at least one window 37 is a quartz window, although the present disclosure is not limited thereto. Rather, housing 34 and window 37 may take many forms. Light source 30 may be advantageously incorporated into and operated in conjunction with the conveyor/transport system 12 of sterilization system 10. The conveyor/transport system 12 may be associated with a wide range of industrial applications, e.g., parenteral pharmaceutical applications, fill and cap product applications, medicinal applications, and the like. In exemplary embodiments, light device 32 of light source 30 is configured and dimensioned to generate and emit/transmit ambient temperature, monochromatic germicidal UV light through the at least one window 37 to the container systems/products 14 entering/passing through the treatment zone 16.

According to exemplary embodiments of the present disclosure, light device 32 is an excimer light device that generally produces 90% of its output within a 10 nm band that can be discretely adjusted across the VUV, UV-A, UV-B and UV-C by changing the rare and/or halogen gases used. In general, efficiencies vary with gas mix and geometry from 10% to >30% with demonstrated input powers from <1 watt to >10 kW. Exemplary flow patterns/arrangements for the introduction and withdrawal of cooling fluids, and exemplary window 37 designs and the like of exemplary light source 30 for use in the disclosed systems and methods are described, disclosed and depicted in commonly assigned patents/patent application Ser. No. 09/805,610 (filed Mar. 13, 2001; published as US 2002-0177118 A1); Ser. No. 10/661,262 (filed Sep. 12, 2003; issued as U.S. Pat. No. 7,282,358); and Ser. No. 10/660,930 (filed Sep. 12, 2003; issued as U.S. Pat. No. 7,057,189), (the "Prior Applications"), the entire contents of which are hereby incorporated by reference in their entireties. For example, an appropriate fluid may be used to maintain the light source 30 at a desired temperature, and/or within a desired temperature range, as described in the Prior Applications. In an exemplary embodiment, water may be used as the heat exchange medium for dissipating/absorbing heat generated through operation of the light source 30. Alternative cooling fluids may be used as well. In one embodiment, the heat exchange medium (e.g., water) forms a part of the dielectric (i.e., electrical) system of light source 30.

In an exemplary embodiment of the present disclosure, light source 30 further includes a guide sleeve (not shown) that is configured and dimensioned to guide the light device 32 into and/or out of the housing 34 to help ensure that the light device 32 does not become damaged during insertion/removal/repair of the light device 32. In one embodiment, the guide sleeve takes the form of a Teflon® guide sleeve, although the present disclosure is not limited thereto. Rather, the guide sleeve may take many forms.

Figures 4, 4A:
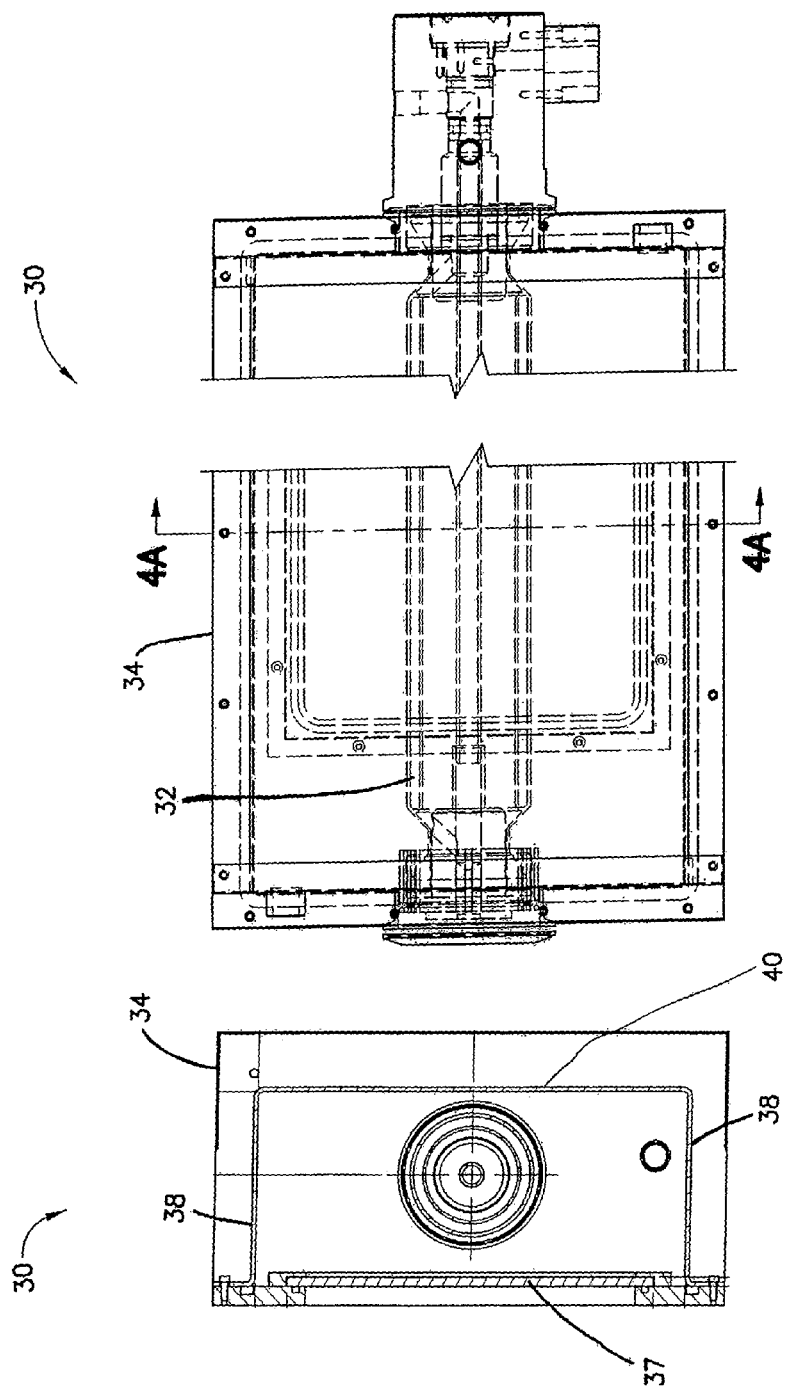
FIG. 4 is a front view of a light source for a sterilization system according to the present disclosure.
FIG. 4A is a sectional view taken substantially along the lines of A-A of FIG. 4 according to the present disclosure.
Figure 5:
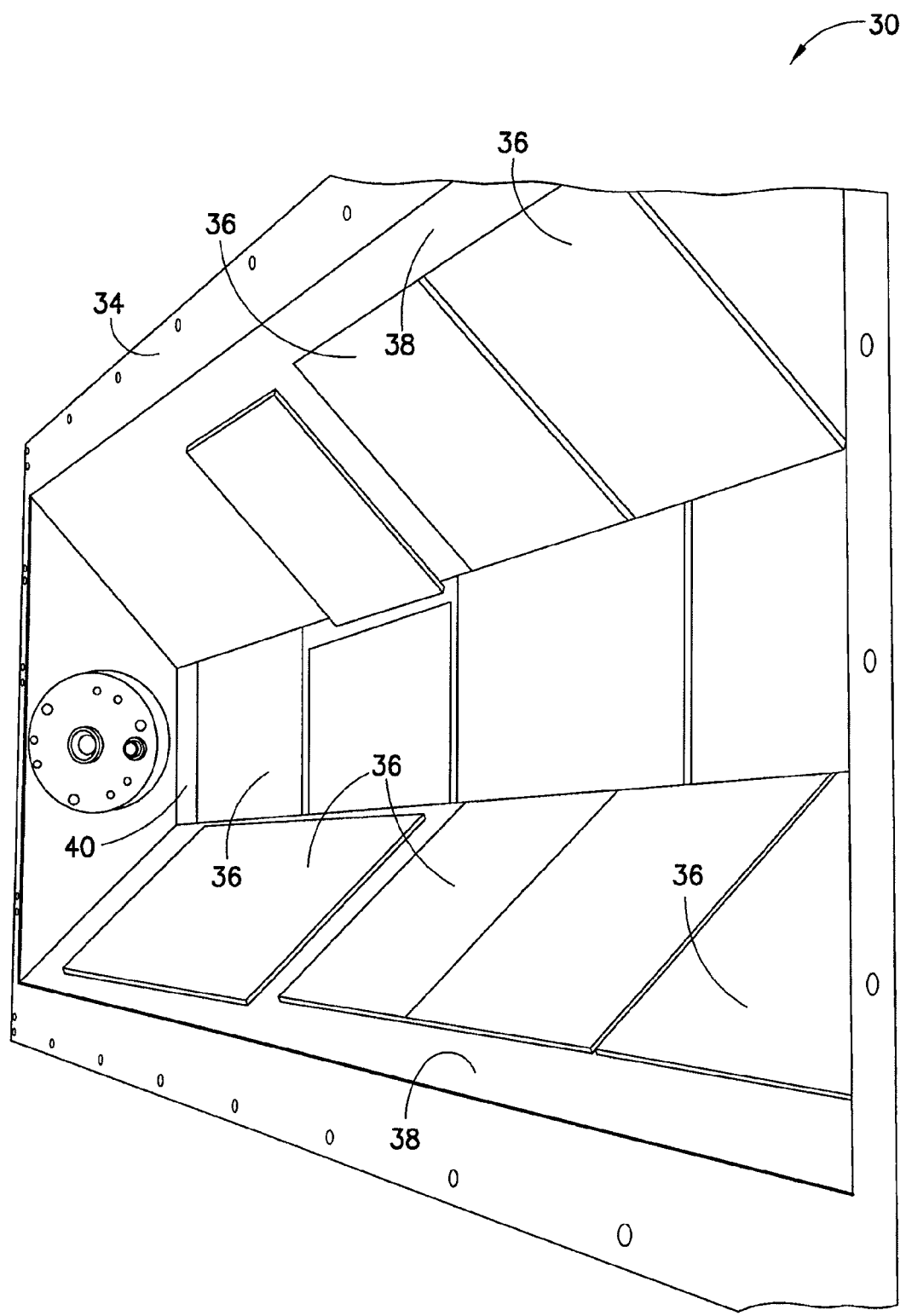
FIG. 5 is a partial front view of a light source (with light device, cover and window removed) for a sterilization system according to the present disclosure.
Figure 5A:
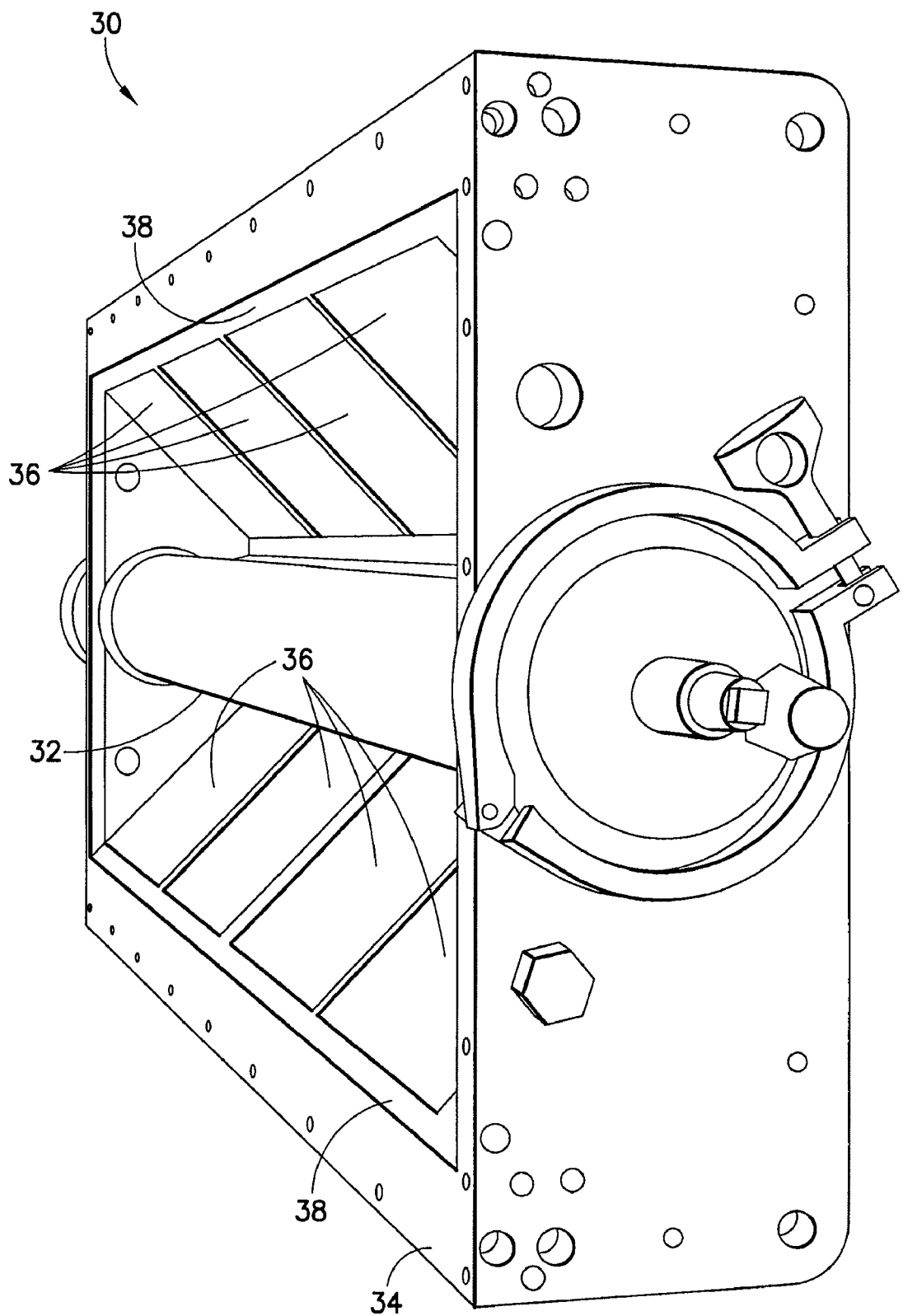
FIG. 5A is a partial front view of a light source (with cover and window removed) for a sterilization system according to the present disclosure.
Figure 6:
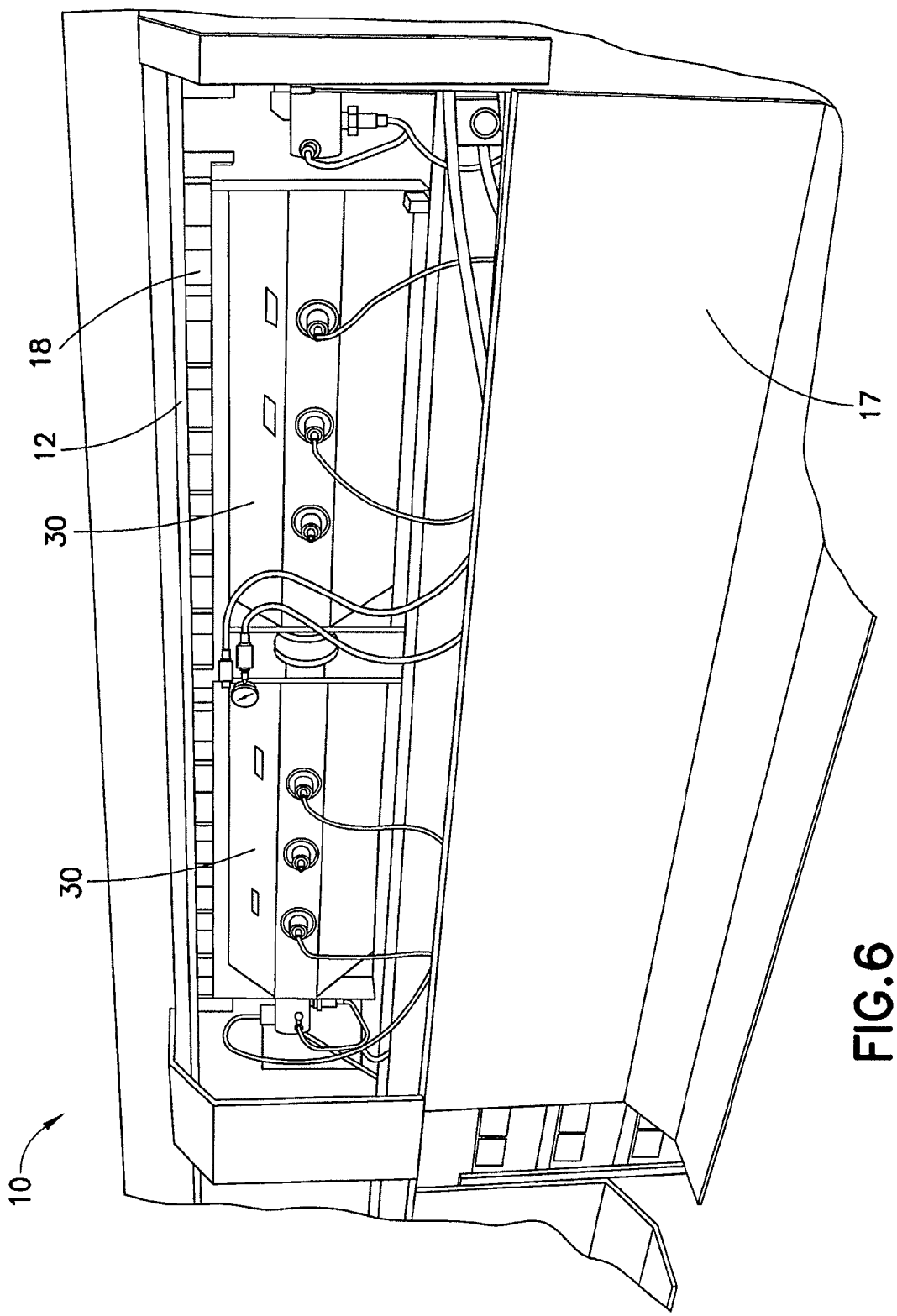
FIG. 6 is a partial view of a sterilization system according to the present disclosure.

With reference to FIGS. 4, 4A, 5 and 5A, exemplary light sources 30 according to the present disclosure are depicted. Exemplary light source 30 includes at least one reflector panel 36. In exemplary embodiments of the present disclosure and as depicted in FIGS. 5 and 5A, light source 30 includes multiple reflector panels 36. Each reflector panel 36 may be releasably secured to the housing 34 of light source 30. In exemplary embodiments, each reflector panel 36 is a reflective and/or coated (e.g., coated, partially coated and/or multiply coated) reflector panel 36. Each reflector panel may be tuned to a desired monochromatic wavelength. The at least one reflector panel 36 of light source 30 may be configured and dimensioned to provide for the dispersion, accentuation and/or filtering of light energy delivered/transmitted by light device 32 to container systems/products 14 in the treatment zone 16. The use of at least one reflector panel 32 in the light source 30 may be effective in delivering/accentuating light from the light source 30 to container systems/products 14 passing through the treatment zone 14 to achieve the desired sterilization results.

In exemplary embodiments of the present disclosure, each reflector panel 36 may be fabricated from quartz, glass, aluminum, coated aluminum and/or stainless steel or the like, although the present disclosure is not limited thereto. In one embodiment, reflector panel 36 is fabricated from glass or quartz. Each reflector panel 36 may be coated, partially coated and/or multiply coated with at least one reflective material, such as, for example, a monochromatic wavelength specific dielectric coating and/or material. Examples of suitable monochromatic wavelength specific dielectric coatings and/or materials include, without limitation, silicon dioxide, hafnium dioxide and the like. Exemplary reflector panel 36 may be coated with at least two reflective materials. In an exemplary embodiment, reflector panel 36 is coated with at least one reflective material (e.g., a monochromatic wavelength specific dielectric coating and/or material), with the reflective material being substantially matched to the monochromatic wavelength generated/transmitted by light source 30 to ensure optimum reflectivity of reflector panel 36, and/or to minimize the loss of reflectivity of reflector panel 36. Similarly, and referring back to FIGS. 1-3 and 6, at least a portion of the interior surface of the cover and/or cover frame 17 of treatment zone 16 is coated with at least one reflective material (e.g., a monochromatic wavelength specific dielectric coating and/or material), with the reflective material being substantially matched to the monochromatic wavelength generated/transmitted by each light source 30 to ensure optimum reflectivity of the interior surface of the cover and/or cover frame 17 of treatment zone 16.

With reference again to FIGS. 4, 4A, 5 and 7, each reflector panel 36 may be coated, partially coated and/or multiply coated with at least one reflective material using, for example, vacuum deposition, vapor deposition, and/or electron beam coating processes, although the present disclosure is not limited thereto. In an exemplary embodiment, reflector panel 36 is coated, partially coated and/or multiply coated with at least two reflective materials using coating processes.

Each reflector panel 36 may be coated, partially coated and/or multiply coated to achieve a desired reflectance level. In exemplary embodiments, each reflector panel 36 is at about a 96% reflectance level for a selected monochromatic wavelength (e.g., the selected wavelength of light source 30). For example, reflector panel 36 may be coated, partially coated and/or multiply coated to achieve about a 96% reflectance level at about 193, 207, 222, 248, 254, 282, 308, 354 and/or 361 nm. Exemplary reflector panel 36 takes the form of a substantially rectangular reflector panel, although the present disclosure is not limited thereto. Rather, reflector panel 36 may take many forms of various geometries/dimensions/sizes, etc. For example, reflector panel 36 may be mosaic.

In an exemplary embodiment and as shown in FIGS. 5 and 5A, light source 30 includes multiple reflector panels 36 releasably secured to the housing 34. Light source 30 may include a desired amount of reflector panels 36.

In one embodiment, light source 30 may include a mosaic or the like of reflector panels 36 releasably secured to the housing 34, wherein each reflector panel 36 is shaped and/or sized for optimum directivity and/or reflectivity of reflected light to each container system/product 14 transported to and/or through the treatment zone 16. In one embodiment, each reflector panel 36 is a formed optic.

As shown in FIGS. 4A, 5 and 5A, housing 34 may include two side walls 38 and a back wall 40. Each side wall 38 may include a desired amount of reflector panels 36, and the back wall 40 may include a desired amount of reflector panels 36. For example, each side wall 38 may include a multiple number of reflector panels 36, and the back wall 40 may include a multiple number of reflector panels 36. Alternatively, one (or both) of the side walls 38 may include at least one reflector panel 36, and the back wall 40 may not include a reflector panel 36. In another embodiment, back wall 40 may include at least one reflector panel 36, and one (or both) of the side walls 38 may not include a reflector panel 36.

In exemplary embodiments, the two side walls 38 may slope inwardly (or outwardly) at a desired angle to meet the back wall 40. In an exemplary embodiment and as shown in FIGS. 5 and 5A, back wall 40 is a substantially straight back wall, and each side wall 38 slopes inwardly at about a 45° angle with respect to the plane of the substantially straight back wall 40 (and/or at about a 45° angle with respect to the central axis of the light device 32) for improved/increased light delivery/reflectance of light source 30. The two side walls 38 may slope inwardly (or outwardly) at any desired angle with respect to the plane of the back wall 40 and/or with respect to the central axis of the light device 32 for delivery/reflectance of light from light source 30. In another embodiment, the two side walls may be placed at about a 90° angle with respect to the plane of the back wall 40 and/or with respect to the central axis of the light device 32. In an alternative embodiment, back wall 40 is a concave or convex back wall, and the two side walls 38 may slope inwardly (or outwardly) at any desired angle with respect to the central axis of the light device 32 to meet the back wall 40.

In an exemplary embodiment and as shown in FIGS. 5 and 5A, back wall 40 is a substantially straight back wall, and each side wall 38 slopes inwardly at about a 45° angle with respect to the plane of the substantially straight back wall 40 (and at about a 45° angle with respect to the central axis of the light device 32) so that the reflector panels located on each side wall 38 are spaced a desired distance on either side of the light device 32 housed in light source 30 for improved/increased light delivery/reflectance of light source 30. For example, each side wall 38 may be configured and dimensioned to meet back wall 40 so that the reflector panels on each side wall 38 are spaced a desired distance on either side (e.g., above and below) from the closest surface of light device 32 housed in housing 34. In an exemplary embodiment, each side wall 38 is configured and dimensioned to meet back wall 40 so that the reflectors panels on each side wall 38 are spaced from about 1" to about 5" on either side (e.g., above and below) from the closest surface of light device 32 housed in housing 34. Alternatively, each side wall 38 may be configured and dimensioned to meet back wall 40 so that at least a portion of the reflector panels located on each side wall 38 are directly behind the light device 32 housed in light source 30.

In exemplary embodiments, sterilization system 10 further includes a control system (not shown). Exemplary control system includes an Allen Bradley PLC and Operator Interface or the like, although the present disclosure is not limited thereto. For example, the control system may be in communication with each light source 30 to control the light source 30 operating parameters. In one embodiment, the control system includes a processor that is programmed to operate the light sources 30 at desired intensity levels and/or time periods. In general, the UV intensity of each light source 30 is monitored and/or controlled to maintain the desired UV dosage. In exemplary embodiments, each light source 30 includes at least one sensor to monitor wavelength and/or to monitor/control intensity. In one embodiment, each light source 30 includes three sensors to monitor wavelength and/or to monitor/control intensity. For example, light source 30 may include one monitoring port for calibration (e.g., with a removable standard). In one embodiment, the wavelength monitor has a neutral density filter built into an end wall of light source 30.

The at least one light source sensor may be linked to the control system. The control system may also be linked to the conveyor/transport system 12 to control/maintain the speed of the container systems/products 14 moving to and/or through the treatment zone 16. For example, the conveyor/transport system 12 may be maintained at a constant speed, or the conveyor/transport system 12 may be operated at variable speeds.

In exemplary embodiments, the speed at which the container systems/products 14 are moved to and/or through the treatment zone 16 may be adjusted so as to achieve the desired energy treatment level based on, for example, a desired residence time/exposure time of each container system/product 14 within the treatment zone 16. The control system may also control and/or modify the process parameters (e.g., UV wavelength, UV intensity, etc.) so as to affect a desired sterilization result, and such processing parameters may be adjusted/selected (either alone or in combination with the rate/residence time of the container systems/products within the treatment zone/exposure tunnel) to achieve desired sterilization results.

In exemplary embodiments, a defined UV intensity range may be established for each container system/product 14 grouping and/or variables (e.g., container size, shape, color, material, product, fill-volume, label copy, amount of ink on containers and/or container reflectance values, container/product spacing in the exposure tunnel, etc.). The control system may automatically adjust the power to each UV light source 30 to maintain each defined UV intensity range for each container system/product 14 grouping and/or variables. For example, the intensity of the light sources 30 utilized in the treatment zone 16 may be adjusted to achieve desired sterilization results. In exemplary embodiments, the UV intensity of each light source 30 may be monitored and/or controlled to maintain a desired UV dosage. In addition, exposure conditions (e.g., conveyor speed, UV wavelength, UV intensity, etc.) can be specific for each container system/product 14 grouping/variables. Furthermore, the UV light sources 30 may be advantageously moved and/or spaced in the treatment zone 16 whether based upon or independent of container system/product 14 groupings/variables. In addition, each UV light source 30 may be operated at the same or different energy intensities to achieve desired sterilization results, whether based upon or independent of container system/product 14 groupings/variables.

In exemplary embodiments, the control system may be configured and adapted to define/establish/control at least one operating parameter of light source 30, or of conveyor/transport system 12. For example, the control system may be configured and adapted to define/establish/control a UV intensity range of each light source 30 for a container system/product 14 grouping (e.g., a container system 14 production run) based upon the amount of printed material or the like (e.g., ink) contained or printed on a certain container system/product 14, and/or based upon the measured reflectance values of the container system/product 14. For example, the control system may automatically adjust/control the power to each UV light source 30 based upon the amount of printed material or the like (e.g., ink) contained or printed on a container system/product 14, and/or based upon the measured reflectance values of the container system/product 14. In an exemplary embodiment, the control system further includes a reflectance measuring unit and/or reflectometer which is configured to measure/detect the reflectance (e.g., surface reflectance) of a container system/product 14. In general, the reflectance of a container system/product 14 may correlate to the amount of printed material or the like (e.g., ink) contained or printed on the container system/product 14. For example, exemplary reflectance measuring unit may measure and/or detect the reflectance of a container system/product 14 by first contacting the container system/product 14 with a light and/or laser, and may then measure/detect the reflectance of the container system/product 14 based upon the reflected light/laser received from the container system/product 14. The reflectance measuring unit and/or reflectometer may then generate and send a signal to the control system to change/adjust/set the UV intensity and/or power output of each light source 30 based upon the measured reflectance of the container system/product 14. For example, the reflectance measuring unit and/or reflectometer may generate the signal by comparing the measured reflectance of the container system/product 14 to a calibration table or the like.

In another embodiment, the reflectance measuring unit and/or reflectometer may generate and send a signal to the control system to change/adjust/set the conveyor/transport system 12 speed, and/or to change/adjust/set the UV wavelength of light source 30 (or some other operating condition) based upon the reflected light/laser received from the container system/product 14.

In exemplary embodiments, the reflectance measuring unit would typically measure the reflectance of a container system/product 14 prior to the container system/product 14 entering the treatment zone 16. Furthermore, the reflectance measuring unit would typically measure the reflectance of a container system/product 14 prior to setting-up the sterilization system 10 for a different production run for each type of container system/product 14 grouping (e.g., for each container system 14 grouping based upon, for example, container size, shape, color, material, etc.).

In exemplary embodiments, after treatment in the treatment zone 16, a Sterilization Assurance Level of at least $10^{-5}$ cfu/ml is achieved for container systems/products 14 that include a panel than may include, without limitation, *Bacillus pumilus* (spore former), *Candida albican* (yeast), lipid and non-lipid virus, *Clostridium sporogenes* (anaerobic spore former), *Alicyclobacillus, Staphylococcus aureus* (vegetative Gram positive), *Pseudomonas aeruginosa* (vegetative Gram negative), *Aspergillus niger* (filamentous fungi), *Mycobacterium terrae*, Porcine Parvo Virus (PPV and B19), *Lysteria, Salmonella, B. atrophaeus, M. luteus* and *S. maltophilia*. This Sterilization Assurance Level may be achieved without materially affecting the overall performance properties of the sterilized container systems/products 14.

In exemplary embodiments, container systems/products 14 which are underdosed or overdosed will be automatically ejected/rejected by the control system, and container systems/products 14 meeting the defined dose requirements will be automatically etched (e.g., laser etched) to indicate sterilization has been affected, in lieu of chemical indicators used with traditional steam sterilization processes.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A sterilization system comprising:
   at least one container system having a container material and a product contained in the container material;
   a treatment zone having at least a first light source and a second light source, each light source having a light device housed in a housing, with each light device configured and dimensioned to generate and transmit substantially ambient temperature and substantially monochromatic light into the treatment zone;
   a transport system having at least one securing means for releasably securing at least one container system to the transport system, the at least one securing means configured and dimensioned to position the at least one container system to establish a product treatment area of product having substantially no air bubbles in the product treatment area;
   wherein the transport system is configured and dimensioned to transport the at least one container system to or through the treatment zone; and
   wherein the at least one container system receives monochromatic light energy from each light source while in the treatment zone to achieve a sterilization effect of the at least one container system.

2. The system of claim 1, wherein the at least one container system is a parenteral pharmaceutical product container system; and
   wherein the product is a parenteral pharmaceutical product or solution.

3. The system of claim 1, wherein the at least one container system is an intravenous bag that is configured and dimensioned to contain from about 5 ml of product or solution to about 5000 ml of product or solution.

4. The system of claim 1, wherein the container material is selected from the group consisting of polyethylene (PE), polypropylene (PP), polyolefins and combinations thereof.

5. The system of claim 1, wherein the monochromatic light is generated at a wavelength that is substantially at a wavelength selected from the group consisting of 193 nm, 207 nm, 222 nm, 248 nm, 254 nm, 282 nm, 308 nm, 354 nm and 361 nm.

6. The system of claim 1, wherein the treatment zone is an exposure tunnel having a cover or cover frame; and
   wherein at least a portion of the interior surface of the cover or cover frame is coated or partially coated with at least one reflective material.

7. The system of claim 1, wherein the at least one securing means releasably secures at least one port of at least one container system to the transport system; and
   wherein the at least one securing means further positions the at least one container system in a substantially vertical position.

8. The system of claim 1, wherein the at least one securing means is configured and dimensioned to minimize or eliminate the shadowing effects from the at least one securing means on the at least one container system.

9. The system of claim 1, wherein the transport system is incorporated in-line and downstream of a container system filling process, and wherein the transport rate of the at least one container system to or through the treatment zone is substantially equal to the filling rate of the container system filling process.

10. The system of claim 1, wherein the sterilization effect of the at least one container system is achieved without negatively affecting the physical properties of the container system or the efficacy of the product contained in the container material.

11. The system of claim 1, wherein the first light source is positioned on one side of the transport system and the second light source is positioned on the other side of the transport system to provide light energy to substantially every surface of the at least one container system while in the treatment zone.

12. The system of claim 1, further including a third, fourth, fifth and sixth light source, each light source configured and dimensioned to generate and transmit substantially ambient temperature and substantially monochromatic light into the treatment zone; and
   wherein the first, third and fifth light sources are positioned on one side of the transport system and the second, fourth and sixth light source are positioned on the other side of the transport system to provide light energy to substantially every surface of the at least one container system while in the treatment zone.

13. The system of claim 1, wherein each light source is further configured and dimensioned to move vertically up or down relative to the central axis of the treatment zone to achieve the sterilization effect of the at least one container system; and wherein at least one light source is moved vertically up or down relative to the central axis of the treatment zone based upon at least one variable of the at least one container system.

14. The system of claim 13, wherein the at least one variable of the at least one container system is selected from the group consisting of container size, fill volume, type of product contained in the container system, color of the container system or product, spacing of the container system or systems entering the treatment zone, label copy, amount of printed material or ink on the container system and reflectance value.

15. The system of claim 1, wherein each light source is further configured and dimensioned to move closer to or farther away from the central axis of the treatment zone to achieve the sterilization effect of the at least one container system; and wherein at least one light source is moved closer to or farther away from the central axis of the treatment zone based upon at least one variable of the at least one container system.

16. The system of claim 1, wherein the light device is an excimer light device.

17. A sterilization system comprising:

at least one container system;

a treatment zone having at least a first light source and a second light source, each light source having a light device housed in a housing, with each light device configured and dimensioned to generate and transmit substantially ambient temperature and substantially monochromatic light into the treatment zone;

a transport system configured and dimensioned to transport the at least one container system to or through the treatment zone;

wherein the at least one container system receives monochromatic light energy from each light source while in the treatment zone to achieve a sterilization effect of the at least one container system;

wherein each housing includes two side walls and a back wall, at least one of the side walls sloping inwardly at an angle to meet the back wall; and wherein the at least one inwardly sloping side wall includes at least one reflector panel releasably secured to the inwardly sloping side wall, the at least one reflector panel configured and dimensioned to provide for the delivery or accentuation of light energy from the light source to the at least one container system while in the treatment zone.

18. The system of claim 17, wherein the at least one container system is a parenteral pharmaceutical product container system.

19. The system of claim 17, wherein the at least one container system is an intravenous bag that is configured and dimensioned to contain from about 5 ml of product or solution to about 5000 ml of product or solution.

20. The system of claim 17, wherein the at least one container system is fabricated from material selected from the group consisting of polyethylene (PE), polypropylene (PP), polyolefins and combinations thereof.

21. The system of claim 17, wherein the monochromatic light is generated at a wavelength that is substantially at a wavelength selected from the group consisting of 193 nm, 207 nm, 222 nm, 248 nm, 254 nm, 282 nm, 308 nm, 354 nm and 361 nm.

22. The system of claim 17, wherein the treatment zone is an exposure tunnel having a cover or cover frame; and wherein at least a portion of the interior surface of the cover or cover frame is coated or partially coated with at least one reflective material.

23. The system of claim 17, wherein the transport system is incorporated in-line and downstream of a container system filling process, and wherein the transport rate of the at least one container system to or through the treatment zone is substantially equal to the filling rate of the container system filling process.

24. The system of claim 17, wherein the sterilization effect of the at least one container system is achieved without negatively affecting the physical properties of the container system or the efficacy of a product contained in the container system.

25. The system of claim 17, wherein the first light source is positioned on one side of the transport system and the second light source is positioned on the other side of the transport system to provide light energy to substantially every surface of the at least one container system while in the treatment zone.

26. The system of claim 17, further including a third, fourth, fifth and sixth light source, each light source configured and dimensioned to generate and transmit substantially ambient temperature and substantially monochromatic light into the treatment zone; and wherein the first, third and fifth light sources are positioned on one side of the transport system and the second, fourth and sixth light source are positioned on the other side of the transport system to provide light energy to substantially every surface of the at least one container system while in the treatment zone.

27. The system of claim 17, wherein each light source is further configured and dimensioned to move vertically up or down relative to the central axis of the treatment zone to achieve the sterilization effect of the at least one container system; and wherein at least one light source is moved vertically up or down relative to the central axis of the treatment zone based upon at least one variable of the at least one container system.

28. The system of claim 27, wherein the at least one variable of the at least one container system is selected from the group consisting of container size, fill volume, type of product contained in the container system, color of the container system or product, spacing of the container system or systems entering the treatment zone, label copy, amount of printed material or ink on the container system and reflectance value.

29. The system of claim 17, wherein each light source is further configured and dimensioned to move closer to or farther away from the central axis of the treatment zone to achieve the sterilization effect of the at least one container system; and wherein at least one light source is moved closer to or farther away from the central axis of the treatment zone based upon at least one variable of the at least one container system.

30. The system of claim 17, wherein the light device is an excimer light device.

31. The system of claim 17, wherein the back wall is a substantially straight back wall; and wherein the at least one inwardly sloping side wall slopes inwardly at about a 45° angle with respect to the plane of the substantially straight back wall.

32. The system of claim 17, wherein the at least one reflector panel is coated or partially coated with at least one reflective material.

33. The system of claim 32, wherein the at least one reflective material is substantially matched to the monochromatic wavelength generated and transmitted by the light source.

34. The system of claim 17, wherein the at least one reflector panel is at about a 96% reflectance level for a selected monochromatic wavelength.

35. A method for controlling a light source comprising:
measuring the amount of printed material on at least one container system with a measuring device;
generating a control signal based upon the measured amount of printed material;
sending the control signal to at least one light source that generates and transmits substantially ambient temperature and substantially monochromatic light;
wherein the control signal establishes or changes at least one operating parameter of the at least one light source.

36. The method of claim 35, wherein the at least one container system is a parenteral pharmaceutical product container system.

37. The method of claim 35, wherein the measuring device measures the reflectance of the at least one container system to generate the control signal.

38. The method of claim 35, wherein the at least one operating parameter of the at least one light source is UV intensity, UV wavelength, or power output.

* * * * *